US006884970B2

United States Patent
Lehman

(10) Patent No.: US 6,884,970 B2
(45) Date of Patent: Apr. 26, 2005

(54) COVER SYSTEM FOR HEATING UNIT

(76) Inventor: Timothy M. Lehman, 11292 Redbud Ct., San Diego, CA (US) 92127

(*) Notice: Subject to any disclaimer, the term of this patent is extended or adjusted under 35 U.S.C. 154(b) by 0 days.

(21) Appl. No.: 10/657,949

(22) Filed: Sep. 9, 2003

(65) Prior Publication Data

US 2004/0045954 A1 Mar. 11, 2004

Related U.S. Application Data

(60) Provisional application No. 60/409,457, filed on Sep. 10, 2002.

(51) Int. Cl.[7] .................... A61B 19/00; A61F 7/00; F27D 11/00
(52) U.S. Cl. .................. 219/432; 219/433; 604/114; 604/291
(58) Field of Search .................. 219/429, 430, 219/433, 435, 438, 432; 604/114, 291; 4/655

(56) References Cited

U.S. PATENT DOCUMENTS

| | | | | |
|---|---|---|---|---|
| 4,967,061 A | * | 10/1990 | Weber et al. | 219/438 |
| 5,129,033 A | * | 7/1992 | Ferrara et al. | 392/447 |
| 5,174,306 A | * | 12/1992 | Marshall | 128/849 |
| 5,435,322 A | * | 7/1995 | Marshall | 128/849 |
| 5,816,252 A | | 10/1998 | Faries, Jr. et al. | |
| 5,857,467 A | * | 1/1999 | Faries et al. | 128/849 |
| 5,950,438 A | * | 9/1999 | Faries et al. | 62/72 |
| 6,003,328 A | * | 12/1999 | Faries et al. | 62/342 |
| 6,087,636 A | * | 7/2000 | Faries et al. | 219/429 |
| 6,087,638 A | | 7/2000 | Silverbrook | |
| 6,091,058 A | * | 7/2000 | Faries et al. | 219/430 |
| 6,202,935 B1 | | 3/2001 | Akkala et al. | |
| 6,255,627 B1 | * | 7/2001 | Faries et al. | 219/430 |
| 2003/0154989 A1 | | 8/2003 | Faries, Jr. et al. | |
| 2003/0172937 A1 | | 9/2003 | Faries, Jr. et al. | |

OTHER PUBLICATIONS

"Synthes®," http://www.synthes-stratec.com/html/PolyMax.137.0.html, 1 page (last printed Aug. 27, 2003).

* cited by examiner

Primary Examiner—Joseph Pelham
(74) Attorney, Agent, or Firm—Shumaker & Sieffert, PA

(57) ABSTRACT

A cover system for a heater unit includes a tray and a cap formed around the mouth of the tray. The tray holds a liquid medium that may be heated to various temperatures. The cap and the tray are coupled to prevent the passage of air and water. As a result, the cover system shields a non-sterilized heater unit from a sterile field in an operating room, thereby preserving the integrity of the sterile field.

28 Claims, 7 Drawing Sheets

COVER SYSTEM FOR HEATING UNIT

This application claims priority from U.S. Provisional Application Ser. No. 60/409,457, filed Sep. 10, 2002, the entire content of which is incorporated herein by reference.

TECHNICAL FIELD

The invention relates to devices used in a sterilized environment.

BACKGROUND

In an operating room, everything is categorized as sterile or non-sterile. The sterile items, which include the surgeon's gloved hands and the instruments that come in contact with the patient, have been made free of microorganisms according to aseptic techniques. To reduce the risk of infection, operating room personnel act to preserve a "sterile field," i.e., the region in the operating room that is properly sterile. Operating room personnel are continually mindful of the sterile field, and conscientiously act to avoid contact between sterile and non-sterile items. By maintaining the integrity of the sterile field, the operating room personnel reduce the risk of transfer of microorganisms from non-sterile areas and items to the surgical wound.

In some circumstances, such as operations involving resorbable implants, it may be expedient to use a heating unit in the operating room. Resorbable implants, such as resorbable thin bone plates, often need to be shaped prior to fixation into the body. The steps involved in shaping these resorbable implants typically include submersing the resorbable implants into a heated water bath whereby the implants become malleable. Once malleable, the implants may be shaped into a desirable configuration.

The implants themselves are sterile, the water (or saline or other solution) in the bath is sterile, and the tray that holds the bath is sterile. The heating unit, however, typically includes electronic components and cannot be sterilized.

SUMMARY

The invention relates to a cover system that may be used to shield off a non-sterilized heater unit in a sterilized environment. The invention provides a cover system for a non-sterilized heater unit comprising a tray and a cap formed around a mouth of the tray. The tray holds a liquid medium that may be heated to various temperatures, and the cap is effective to prevent exposure of the non-sterilized heater unit to a sterilized environment. In one embodiment, the cover system is a single unit and is autoclavable, i.e., sterilizable in an autoclave.

The cover system is sized to fit over a heater unit, and the contours of the cover system may depend upon the contours of the heater unit being covered. In some embodiments of the invention, the cap is transparent or translucent, allowing instrumentation on the heater unit to be visible even when the heating unit is covered.

The cap and the tray may be coupled together by any of several techniques. They may, for example, be a single-piece construction, or they may be permanently joined by molding or another technique. The cap and the tray may also be coupled mechanically with a tight junction, and sealed with a sealant. With each of these techniques, the tray and the cap can be coupled to prevent the passage of air and water. A hermetic seal between the tray and the cap preserves the sterile field by physically separating a significant portion of the non-sterile heating unit from the sterile field. The hermetic seal further protects the heating unit in the event of spillage of water from the tray.

The cover system optionally includes a sterile drape. Moreover, in some embodiments of the invention, the cap includes a lip that can support a sterile drape. In that case, the drape effectively expands the cover system, thereby providing an added measure of isolation of the heater unit from the sterile field.

In one embodiment, the invention is directed to a cover system comprising a tray to hold a liquid to be heated by a heater unit. The tray includes a mouth. The cover system further includes a cap coupled to the tray, with the cap extending around the mouth of the tray and the cap being sized to cover at least a portion of the heater unit. The tray may be made of a material such as stainless steel, and the cap may be made of medical grade plastic. Several different materials may also be used to make up the cover system, however. The cover system may also include a drape, made of a material such as silicone.

In another embodiment, the invention is directed to a cover system comprising a tray and a cap coupled to the tray. The tray includes a mouth. The cap extends around the mouth and is sized to cover at least a portion of a heater unit. In accordance with the invention, the tray and the cap are coupled to prevent the passage of air and water.

In a further embodiment, the invention presents a system comprising a heater unit and a cover system sized to cover at least a portion of the heater unit. The cover system includes a tray and a cap coupled to the tray, and the tray and the cap are coupled to prevent the passage of air and water.

The invention may provide one or more advantages. In particular, the cover system allows the tray to be brought in contact with the heating element of the heater unit. As a result, the heater unit can transfer adequate heat to the tray without compromising the sterile field. It is unnecessary to have an intervening sterile guard between the tray and the heating element. The hermetic seal or tight junction between the tray and the cap prevents the passage of air and water, thereby preserving the sterile field and protecting the heating unit from spills.

The cover system may be easily sterilizable and reusable. The cover system can be easily placed over the heater unit and requires no complicated assembly. The addition of an optional drape can further isolate the heater unit from the sterile field.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
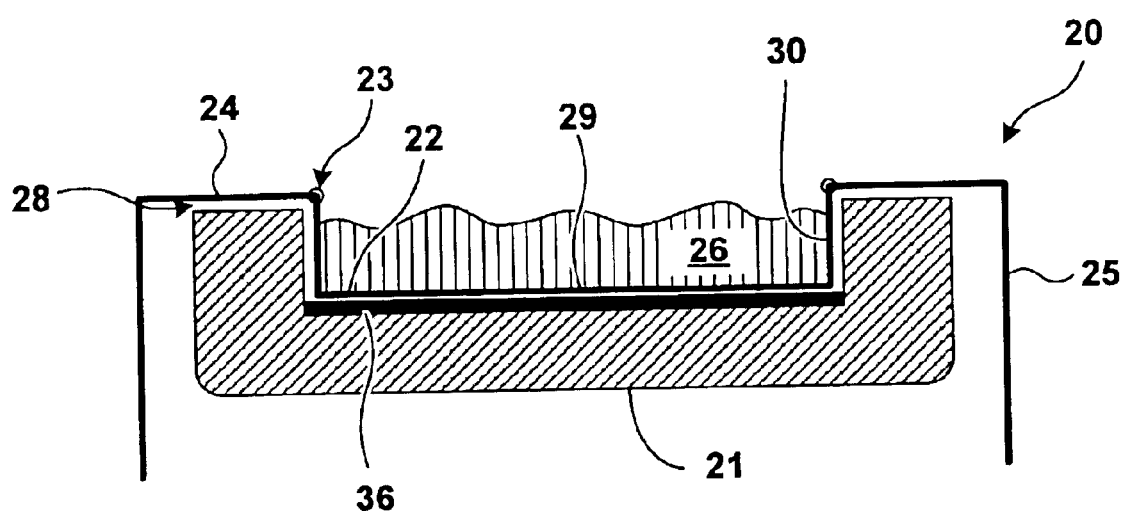
FIG. 1 is a cross-sectional side view of a heater unit and a cover system.

Reference will now be made in detail to the presently preferred embodiments of the invention, examples of which are illustrated in the accompanying drawings. Wherever possible, the same or similar reference numbers are used in the drawings and the description to refer to the same or like parts. It should be noted that the drawings are in simplified form and are not to precise scale. In reference to the disclosure herein, for purposes of convenience and clarity only, directional terms, such as, top, bottom, left, right, up, down, over, above, below, beneath, rear, and front, are used with respect to the accompanying drawings. Such directional terms should not be construed to limit the scope of the invention in any manner.

Although the disclosure herein refers to certain illustrated embodiments, it is to be understood that these embodiments are presented by way of example and not by way of limitation. The intent of the following detailed description, although discussing exemplary embodiments, is to be construed to cover all modifications, alternatives, and equivalents of the embodiments as may fall within the spirit and scope of the invention as defined by the appended claims.

An effective cover system for a heater unit, such as a surgical heater unit, is described. In a broad embodiment, the cover system comprises a tray and a cap formed around a mouth of a tray. Preferably, the cover system can snugly fit over a heater unit, so as to effectively cover the heater unit. A variety of heater units may be used in accordance with this invention. Generally, the heater unit has a heating surface on top of the heater unit to heat up the tray. In one embodiment, a heater unit used in accordance with this invention is capable of heating a liquid medium in the tray to a temperature of about 60 to about 70 degrees Celsius. U.S. Pat. No. 6,202,935 describes one exemplary heating unit, the disclosure of which is incorporated in its entirety herein by reference.

FIG. 1 is a cross-sectional schematic view of a cover system 20 and a heater unit 21. The cover system 20 is shown in FIG. 1 comprising a tray 22 and a cap 24. As will be described below, tray 22 and cap 24 may be constructed of different materials, but are coupled to form a single piece cover system. The tray 22 in the illustrated embodiment comprises a base 29 and a side wall 30 running up from the base 29 to hold a liquid medium 26 therein. The base 29 of the tray 22 may be of any shape, such as square, rectangular, oval or irregular. In one embodiment, the base 29 is rectangular shaped, and the side wall 30 extends between the four corners of the base 29. An open end of the side wall 30 forms a mouth of the tray 22. In another embodiment, the base 29 curves into the side walls 30 without corners, thereby forming the mouth. The mouth of tray 22 receives the sterile water or saline solution used in the heated water bath.

The cap 24 is formed around, or extends from, the mouth of the tray 22 so as to effectively cover the heater unit 21. For example, from the mouth of the tray 22, the cap 24 extends over the heater unit 21 and drops down the side of the heater unit 21. In one embodiment, the cover system 20 snugly fits over the heater unit 21, and the tray 22 rests against or in close proximity to a heating pad 36 or other heating element of the heater unit. The cap 24 need not contact heater unit 21, however. As shown in FIG. 1, an air gap 28 may separate the cap 24 from the heater unit 21. The air gap 28 provides some thermal insulation so that the cap 24 stays cool while the heating pad 36 heats tray 22.

The tray 22 of the cover system 20 may be constructed from any material effective to transfer heat from the heater unit 21 to the liquid medium 26, such as water, contained by the tray 22. In one embodiment, the tray 22 is able to effectively transfer heat to the liquid medium 26 contained therein. For example, a tray 22 in accordance with the invention is capable of transferring adequate heat from the heater unit 21 below to heat a liquid medium 26 to about 60 through about 70 degrees Celsius in less than about 15 minutes, and preferably less than about 10 minutes. Preferably, the tray 22 does not rust and does not melt while transferring the required heat to the liquid medium 26. In one embodiment, the tray 22 is stable to repeated sterilization processes, such as autoclaving and gamma radiation.

Furthermore, contaminants, such as microbes and the like, cannot permeate from one surface of the tray 22 to the other. Preferably, the tray 22 of the invention is autoclavable for sterilization. In one embodiment, the tray is constructed from stainless steel, the like, or mixtures thereof. In one embodiment, the tray 22 may have a dimension of 5⅛ inches (13.0 cm) by 6 9/16 (16.7 cm) inches by 4 inches (10.1 cm). Preferably, the tray may hold about 1 to about 2 liters, and preferably about 1.5 liter, of the liquid medium 26.

The cap 24 of the cover system 20 may be constructed from any material effective to seal off any contaminants on the surface of the heater unit 21. Preferably, the cap 24 does not rust and does not melt when placed over the heater unit 21 in operation. In one embodiment, the cap 24 is stable to repeated sterilization processes, for example autoclaving and gamma radiation. In another embodiment, the cap 21 is constructed from the same material as that of the tray 22, such as stainless steel. In one embodiment, the cap 24 is constructed from a material different from that of the tray, such as an autoclavable plastic. An example of an autoclavable plastic is Ultem plastics or resins, commercially available from GE Plastics of Pittsfield, Mass. In some embodiments, the autoclavable plastic is transparent or translucent, allowing medical personnel to be able to see instrumentation on the heater unit 21, such as a temperature readout.

In one embodiment, the tray 22 and the cap 24 are molded as a single unit cover system 20. In one embodiment, the cover system 20 may be constructed from deep molding a deep drawn stainless steel tank into a tinted (smoked) plastic cap. In another embodiment, the tray 22 and the cap 24 are removably attached together to form the cover system 20. For example, the mouth of the tray 22 meets and attaches with the cap 24, and a tight junction 23 is formed therebetween. By tight junction, it is meant that a contaminant cannot pass through the interface where the tray 22 and the cap 24 meet. The use of any known means of attachment between the tray 22 and cap 24 is possible, such as an attachment through use of an adhesive, or riveting, clamping, snapping, bolting or latching. A sealant, such as silicone seal or a gasket, may be employed to create or improve a tight junction 23 between the tray 22 and the cap 24. In particular, the sealant may be deployed between the tray 22 and the cap 24 to create or to assure an airtight and watertight hermetic seal.

Whether formed as single piece or joined with a tight junction, the tray 22 and cap 24 are coupled by a hermetic seal that prevents the passage of air and water. The hermetic seal serves at least two functions. First, the hermetic seal preserves the sterile field by physically separating the non-sterile heating unit 21 from the sterile field. Second, the hermetic seal protects the heating unit 21. In the event water from tray 22 spills, water will not penetrate the hermetic seal and get into the heating unit 21, and possibly causing damage to the electronic components of the heating unit 21. In a preferred embodiment, the cover system 20 comprising the tray and the cap is sterilized prior to use.

Figure 2:
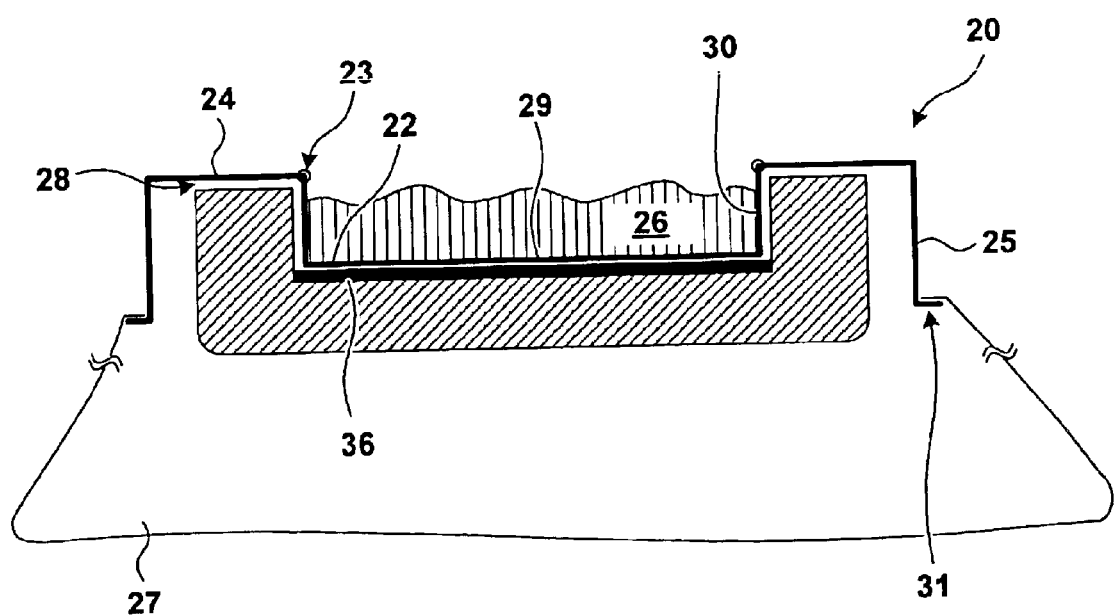
FIG. 2 is a cross-sectional side view of a heater unit and a cover system similar to FIG. 1, but further comprising a lip and a drape attached to the lip.

Referring to the cross-sectional schematic view shown in FIG. 2, the cap 24 preferably comprises a lip 31 surrounding the mouth of the cap 24. In other words, the cap includes an outer perimeter that extends around the heating unit 21, and the outer perimeter includes the lip 31. A drape 27 can be attached to the lip 31 of the cap 24 by various means, such as hook and loop fasteners including Velcro®. In such an embodiment, the lip 31 may be reduced or altered in size or shape, or eliminated. In a preferred embodiment of the invention, the drape 27 comprises an opening which is shaped to approximate the inner circumference of the lip 31, so that the opening of the drape 27 can fit around the cap 24 and slide down to rest on the lip 31. A circumference of the outer edge (measured in a radial direction) of the lip 31 is preferably slightly greater than a circumference of the opening of the drape 27, so that the drape 27 is caught on the lip 31 to prevent the drape 27 from sliding further down and off of the lip. In one embodiment, the drape 27 is effective to cover the area surrounding the heater unit 21.

Figure 3:
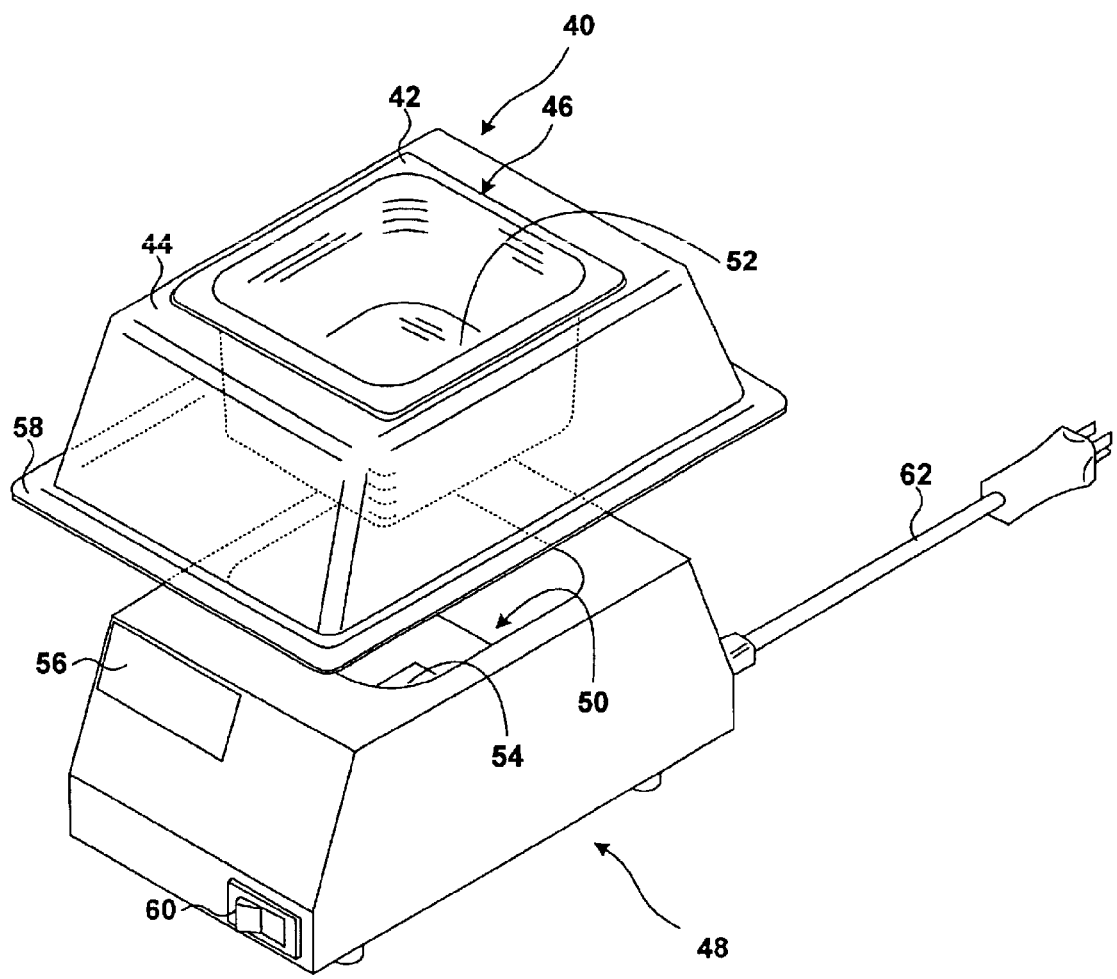
FIG. 3 is a perspective drawing illustrating a cover system separated from a heater unit.

FIG. 3 is a perspective view of an embodiment of the invention. A cover system 40 comprises a tray 42 and a cap 44. The cap 44 is formed around the mouth of the tray 42, and the junction 46 between the tray 42 and the cap 44 comprises a hermetic seal that prevents the passage of air and water.

The cover system 40 is sized to fit over a heater unit 48. In particular, the cover system 40 is dimensioned so that the tray 42 rests in a well 50, and the base 52 of the tray 42 rests against or is in close proximity to a heating pad 54 of the heater unit 48. In addition, the cap 44 follows the general contours of the heater unit 48. The cap 44 may be sized to touch the heater unit 48, or may be sized to be separated from the heater unit 48 by an air gap when the tray 42 rests in the well 50.

Figure 4:
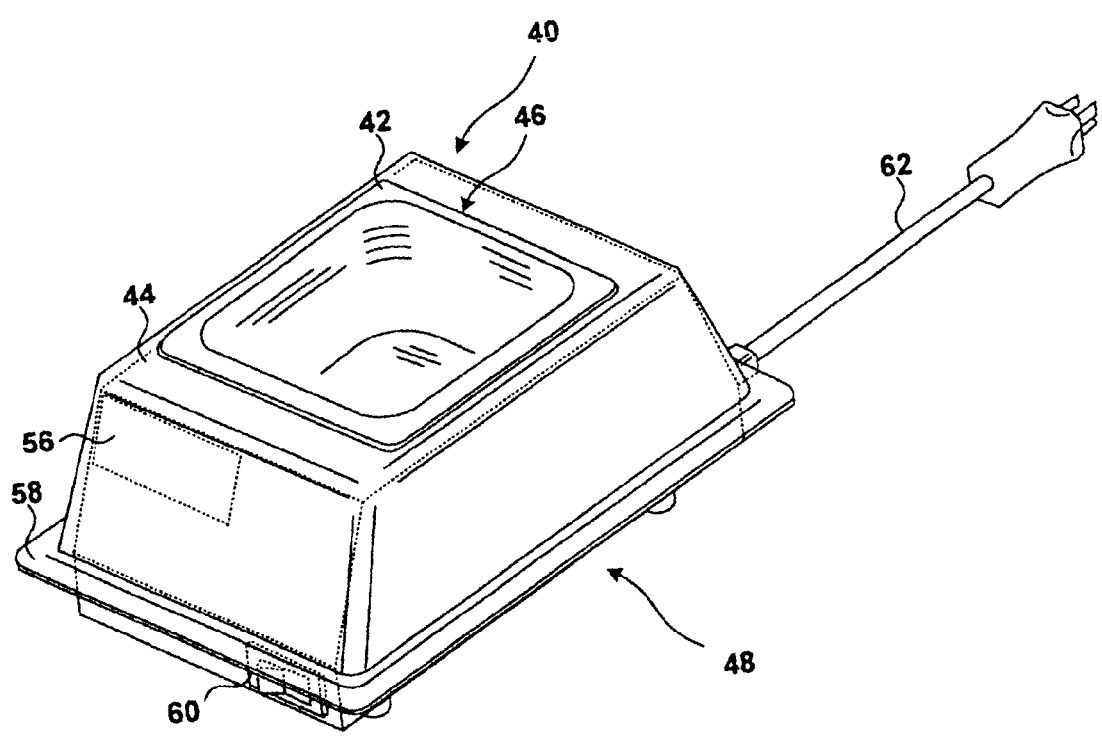
FIG. 4 is a perspective drawing illustrating the cover system and heater unit shown in FIG. 3, with the cover system in place over the heater unit.

FIG. 4 is a is a perspective view of the embodiment of the invention shown in FIG. 3, with the cover system 40 covering the heater unit 48. In the embodiment shown in FIG. 4, the cap 44 is transparent or translucent. Accordingly, instrumentation on the heater unit 48, such as a temperature readout 56, is visible through the cap 44 when the cover system 40 covers the heater unit 48.

The embodiment of the cover system 40 shown in FIGS. 3 and 4 provides some isolation of the heating unit 48 from the sterile field. The hermetic seal 46 between the tray 42 and the cap 44 preserves the sterile field by physically separating a significant portion of the non-sterile heating unit 48 from the sterile field. The hermetic seal 46 further protects the heating unit 48 in the event water from the tray 42 spills.

Figure 6:
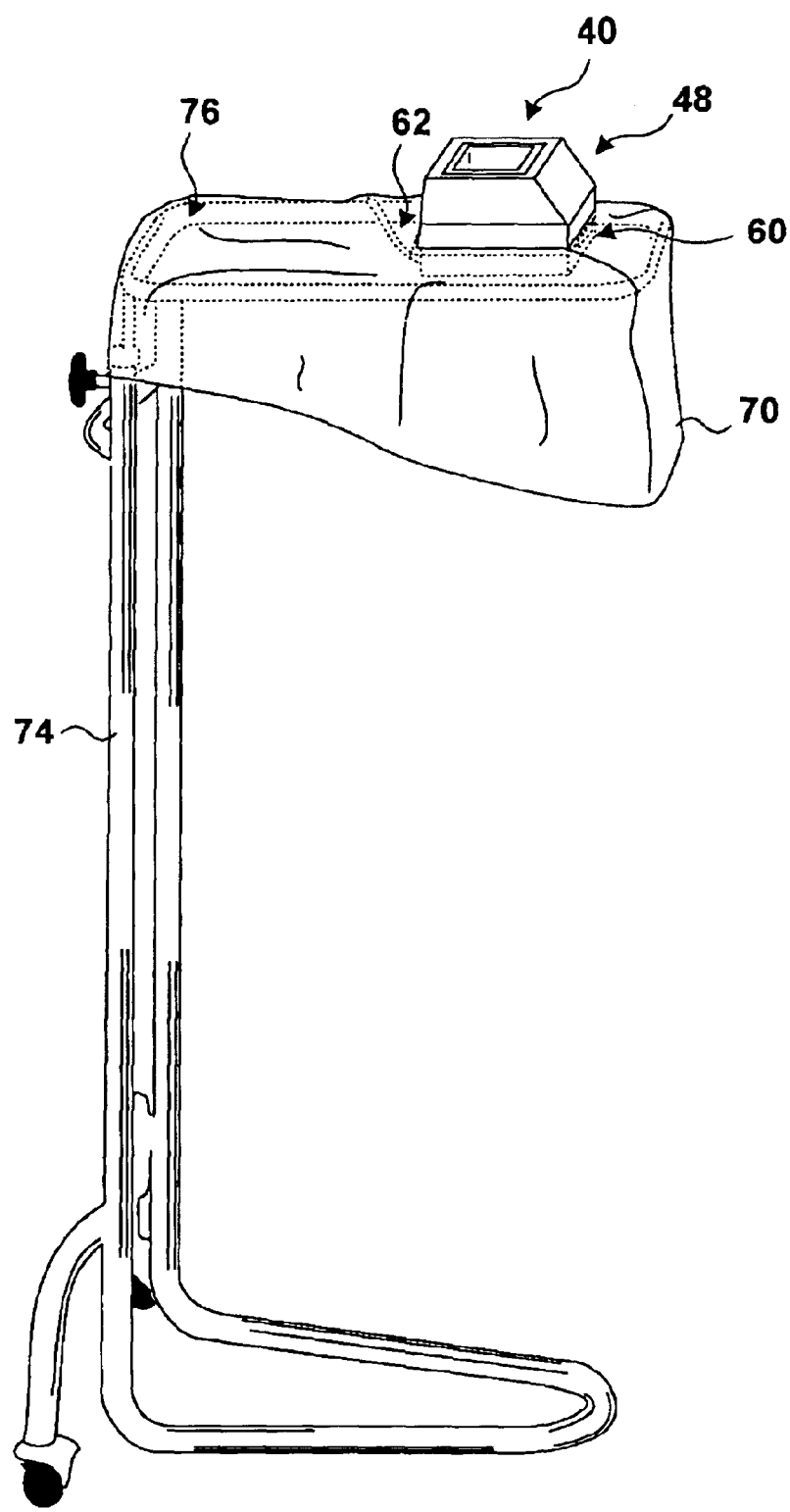
FIG. 6 is a perspective drawing illustrating a stand, with a heater unit, cover system and drape deployed on the stand.

As shown in FIGS. 3 and 4, the cap 44 comprises a lip 58, which can support a drape as shown below. As shown in FIG. 4, the lip 58 does not hinder access to an on-off switch 60 or a power cord 62 of the heater unit 48 when the cover system 40 covers the heater unit 48. The lip 58 does not isolate the on-off switch 60 or the power cord 62 from the sterile field, however. When the drape is in place as shown in FIG. 6 below, the on-off switch 60 and the power cord 62 are isolated from the sterile field.

Figure 5:
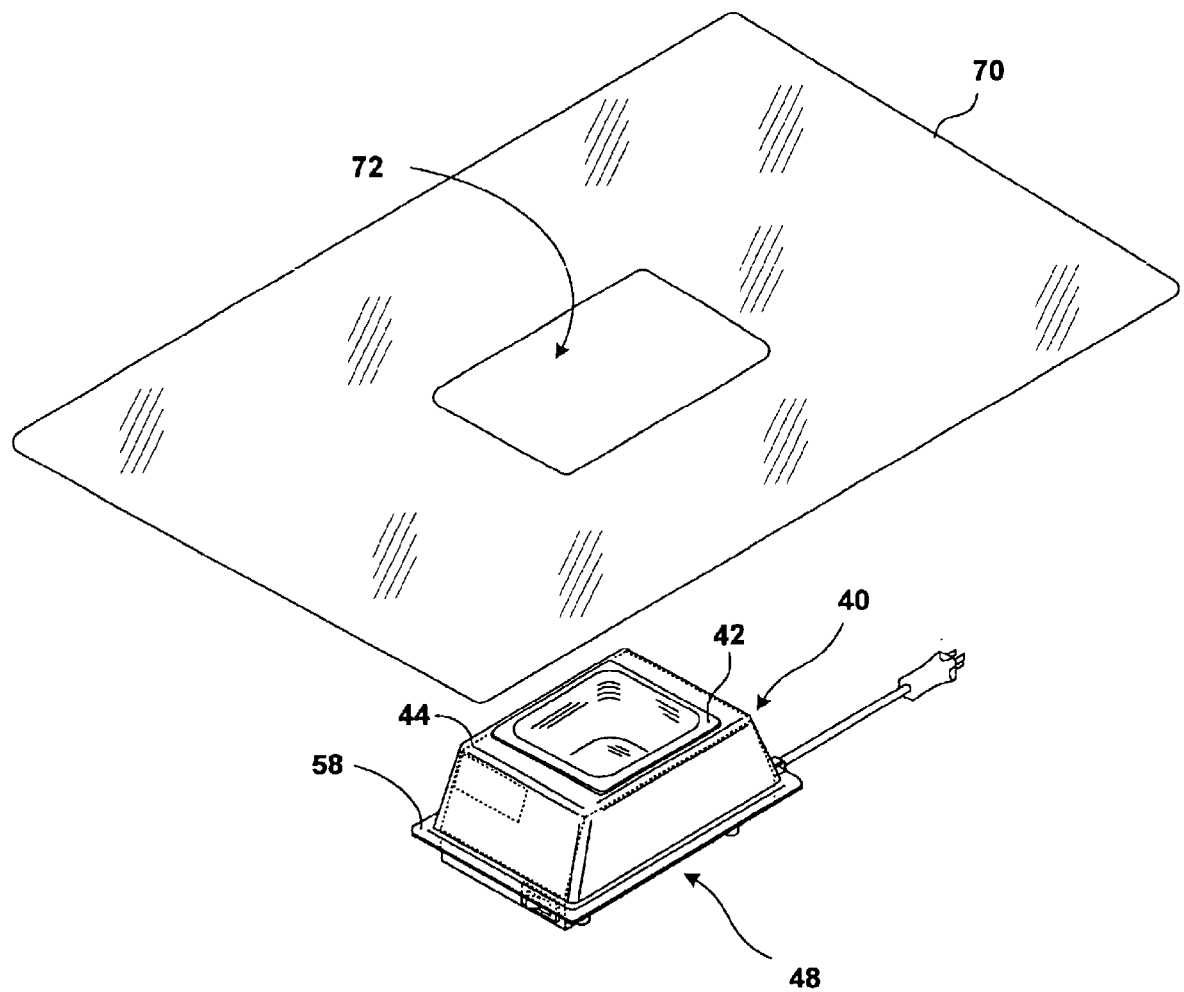
FIG. 5 is a perspective drawing illustrating the cover system and heater unit shown in FIGS. 3 and 4, with the cover system in place over the heater unit and a drape stretched above the cover system and heating unit.

FIG. 5 is a perspective view of the cover system 40 and the heater unit 48 shown in FIGS. 3 and 4, along with a drape 70. The drape 70 includes an opening 72 that is shaped to approximate the inner circumference of the lip 58, so that the opening 72 of the drape 70 can fit around the cap 44 and rest on the lip 58. The drape 70 is flexible so that it can drape over nearby equipment. The drape 70 may also be transparent or translucent, so that the covered equipment, or parts thereof, can be easily seen.

The drape 70 is made of sterilizable material. A variety of materials may be used for the drape 70. In one embodiment, the drape 70 comprises a thin, textured silicone membrane. The drape 70 may be sterilized in advance, and brought into the operating room in a sterile container. The drape 70 may be re-sterilized or discarded after use.

The drape 70 may be of any dimension. As shown in FIG. 5, the drape 70 can extend outward from the cap 44, thereby covering heater unit 48 to a greater degree. In one embodiment, the drape 70 extends about one foot to two feet (30 to 61 cm) radially outward from the opening 72, but the dimensions of the drape 70 may vary. Although FIG. 5 shows the drape 70 as being substantially rectangular with the opening 72 in the approximate center of the drape 70, the drape 70 may be any shape and the opening 72 may be located anywhere.

FIG. 6 is a perspective view showing an exemplary deployment of the invention. In an operating room, the heater unit 48 may be placed on a "Mayo stand" 74, i.e., heater unit 48 may be supported on a tabletop 76 of the stand 74. The cover system 40 covers the heating unit 48 and at least partially isolates the heating unit 48 from the sterile field. The drape 70 is deployed to cover the heater unit 48 and at least portions of the power cord 62 and the stand 74. In the embodiment shown in FIG. 6, the drape 70 extends about one foot (30 cm) below the tabletop 76 of the stand 74. When cover system 40, heater unit 48 and drape 70 are deployed as shown in FIG. 6, a sterile person in the operating room is less likely to become non-sterile by inadvertently bumping stand 74.

In this configuration, the drape 70 isolates the on-off switch 60 from the sterile field. The drape 70 does not prevent operating room personnel from having access to the on-off switch 60, however. Non-sterile personnel can access the on-off switch 60 by reaching under the drape 70 without invading the sterile field. Sterile personnel can access the on-off switch 60 by depressing the on-off switch 60 through drape 70.

Figure 7:
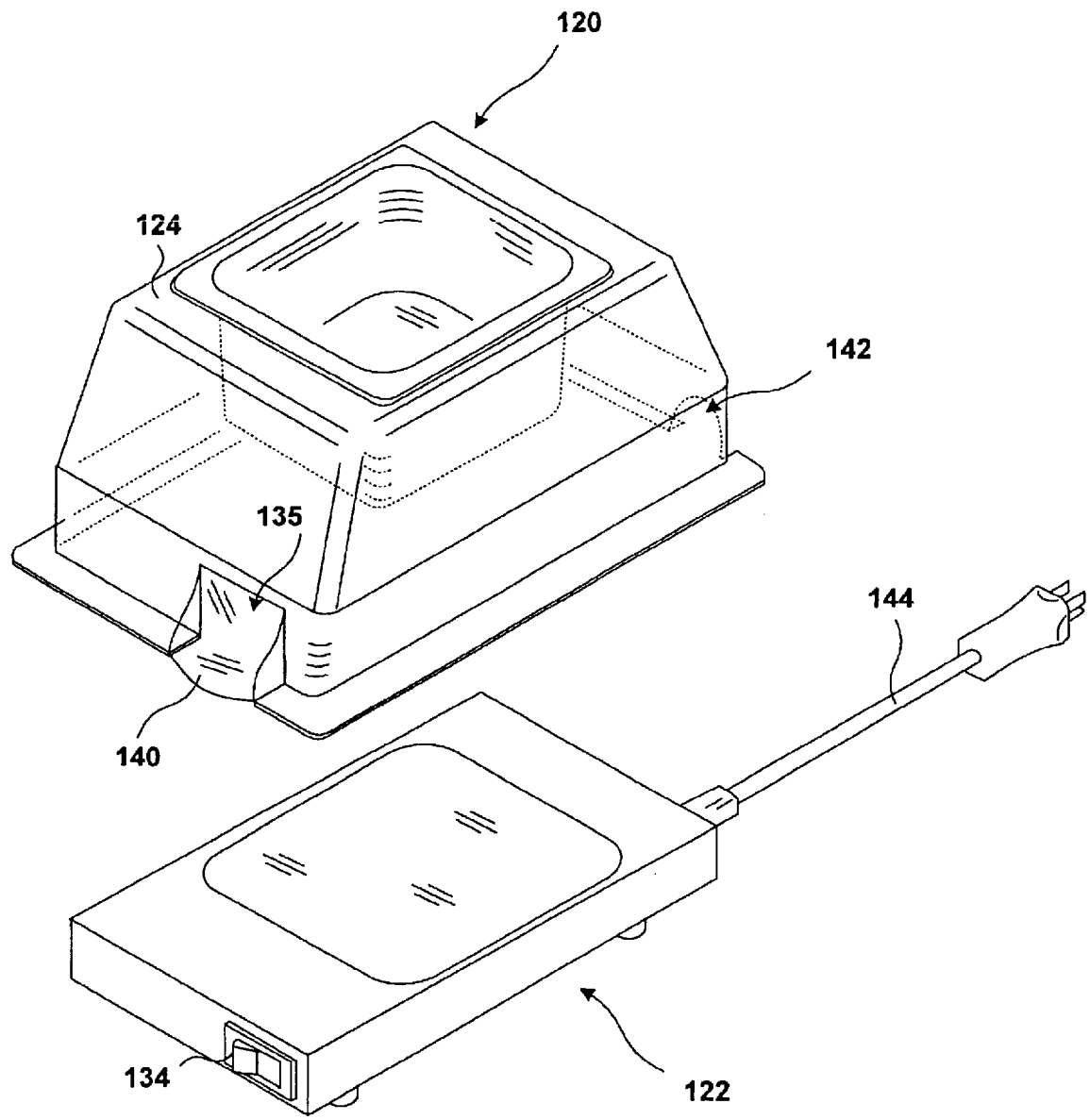
FIG. 7 is a perspective drawing illustrating an alternate embodiment of a cover system and a heater unit.

The cover system of the invention may be shaped as to accommodate for the various features of the heater unit it is covering. For example, FIG. 7 shows a cover system 120 sized and configured for a different model of heating unit 122. In the embodiment of the cover system shown in FIG. 7, the cap 124 includes a cut out 135 to provide accessibility to an on/off switch 134 on the heater unit 122. The cut out 135 may be patched over by a soft cover 140 to allow for manipulation of the on/off switch 134 through the soft cover 140. Preferably, the soft cover 140 is a plastic, and more preferably a transparent plastic. A similar cut out 142 may be available to allow access for other items, such as the power cord 144 of the heater unit 122. Other cut outs may be available for viewing of a temperature gauge or other instrument on the heater 122, for example. A drape can be added to optionally cover any cut outs and corresponding elements of heater unit 122 that protrude through such cut outs.

The invention may provide one or more advantages. In particular, the cover system allows the tray to be brought in contact with the heating element of the heater unit. As a result, the heater unit can transfer adequate heat to the tray without compromising the sterile field. The invention can avoid the need for an intervening sterile guard between the tray and the heating element. The hermetic seal or tight junction between the tray and the cap prevents the passage of air and water, thereby preserving the sterile field and protecting the heating unit from spills.

The cover system may be easily sterilizable and reusable. The cover system may be easily placed over the heater unit and typically requires no complicated assembly. The addition of an optional drape can further isolate the heater unit from the sterile field.

While this invention has been described with respect to various specific examples and embodiments, it is to be understood that the invention is not limited thereto and that it can be variously practiced. A cover system may be customized to the conformation of a particular kind of heater unit, for example, so the invention is not limited to the specific conformations shown in the figures.

Because a cover system may be dimensioned for a particular kind of heater unit, the cover system may include one or more coupling elements that temporarily couple the cover system to the heater unit. Snaps, hasps, springs, ribs, notches, grooves and clasps are examples of coupling elements. A cover system may include leaf springs, for example, that mate to grooves on the heater unit, or vice versa. With coupling elements such as these, the cover system can snap into place in the heater unit. Not only do coupling elements help secure the cover system to the heater, the coupling elements may also provide audible or tactile feedback indicating to a user that the cover system is properly in place.

Furthermore, the cover system need not be formed from a tray and cap of different materials, but may be formed as a single-piece construction. The drape may be included as an integral part of the cover system, or may be omitted completely.

The cover system need not include a lip to support a drape. As shown in FIGS. 3–7, a cover system may include tapered sides, and the opening of the drape may be sized to slide part way down the sides.

The invention need not be constructed with the specific materials described herein. For example the tray need not be made of stainless steel, but may be made of another metal, or may be made of plastic or another heat-conductive material. The cap need not be formed from a plastic or a polymer, but may be formed from metal or any other material. These and other embodiments are within the scope of the following claims.

What is claimed is:

1. A cover system comprising:
   a metallic tray to hold a liquid to be heated by a heater unit, the tray including a mouth; and
   a cap coupled to the tray, the cap extending around the mouth and sized to cover at least a portion of the heater unit.

2. The cover system of claim 1, further comprising a hermetic seal where the cap is coupled to the tray.

3. The cover system of claim 1, wherein the tray and the cap are formed as a single unit.

4. The cover system of claim 1, wherein the tray is made of stainless steel.

5. The cover system of claim 1, wherein the cap is made of plastic.

6. The cover system of claim 1, wherein the cap comprises at least one of a translucent material and a transparent material.

7. The cover system of claim 1, wherein the heater unit comprises a heating element, the cover system configured to place the tray in contact with the heating element when the cap covers at least a portion of the heater unit.

8. The cover system of claim 1, wherein the cap includes an outer perimeter, the outer perimeter comprising a lip.

9. The cover system of claim 8, further comprising a drape coupled to the lip.

10. The cover system of claim 1, further comprising a drape extending outwards from the cap.

11. The cover system of claim 10, wherein the drape is made of silicone.

12. The cover system of claim 10, wherein the drape comprises at least one of a translucent material and a transparent material.

13. The cover system of claim 1, further comprising a coupling element to temporarily couple the cover system to the heater unit.

14. A cover system comprising;
    a tray comprising a mouth; and
    a cap coupled to the tray, the cap extending around the mouth and sized to cover at least a portion of a heater unit and including an outer perimeter, the outer perimeter comprising a lip,
    wherein the tray and the cap are coupled to prevent the passage of air and water.

15. The cover system of claim 14, wherein the tray and the cap are formed as a single unit.

16. The cover system of claim 14, further comprising a drape coupled to the lip.

17. The cover system of claim 14, further comprising a drape extending outwards from the cap.

18. The cover system of claim 14, wherein the tray and the cap are coupled by at least one of molding, adhesive, riveting, clamping, snapping, bolting and latching.

19. The cover system of claim 18, further comprising a sealant interposed between the tray and the cap.

20. The cover system of claim 14, further comprising a coupling element to temporarily couple the cover system to the heater unit.

21. A system comprising:
    a heater unit; and
    a cover system sized to cover at least a portion of the heater unit, the cover system comprising:
    a tray;
    a cap coupled to the tray; and
    a drape extending outwards from the cap;
    wherein the tray and the cap are coupled to prevent the passage of air and water, and wherein the heater unit includes a first coupling element and the cover system includes a second coupling element, the first and second coupling elements configured to mate to temporarily couple the cover system to the heater unit.

22. The system of claim 21, wherein the cap and the heater unit are sized to define an air gap between the cap and the heater unit when the cover system covers at least a portion of the heater unit.

23. A cover system comprising:
    a tray to hold a liquid to be heated by a heater unit, the tray including a mouth; and
    a cap coupled to the tray, the cap extending around the mouth and sized to cover at least a portion of the heater unit;
    wherein the tray and the cap are stable to repealed sterilization processes.

24. The cover system of claim 23, wherein the tray and the cap are formed as a single unit.

25. The cover system of claim 23, wherein the cap comprises at least one of a translucent material and a transparent material.

26. The cover system of claim 23, wherein the heater unit comprises a heating element, the cover system configured to place the tray in contact with the heating element when the cap covers at least a portion of the heater unit.

27. The cover system of claim 23, further comprising a drape attached to the cap.

28. The cover system of claim 23, further comprising a coupling element to temporarily couple the cover system to the heater unit.

* * * * *